(12) United States Patent
Sideris

(10) Patent No.: US 6,893,878 B2
(45) Date of Patent: May 17, 2005

(54) CENTRIFUGAL SPECTROMETER

(75) Inventor: Dimitrios Sideris, London (GB)

(73) Assignee: Deltadot Limited, London (GB)

( * ) Notice: Subject to any disclaimer, the term of this patent is extended or adjusted under 35 U.S.C. 154(b) by 103 days.

(21) Appl. No.: 10/074,297

(22) Filed: Feb. 13, 2002

(65) Prior Publication Data

US 2003/0113926 A1 Jun. 19, 2003

(30) Foreign Application Priority Data

Dec. 18, 2001 (GB) .............................................. 0130235

(51) Int. Cl.⁷ .............................................. G01N 27/26
(52) U.S. Cl. ......................... 436/177; 422/45; 204/545; 204/547
(58) Field of Search .......................... 422/45; 204/450, 204/545, 547; 436/177, 178

(56) References Cited

U.S. PATENT DOCUMENTS

| | | | |
|---|---|---|---|
| 3,395,093 A | | 7/1968 | Liberti |
| 3,556,967 A | | 1/1971 | Anderson |
| 4,008,135 A | * | 2/1977 | Gazda ........................ 205/755 |
| 4,432,849 A | | 2/1984 | Saito ...................... 204/180 R |
| 4,726,904 A | | 2/1988 | Ayers |
| 5,298,143 A | * | 3/1994 | Ivory et al. .................. 204/543 |
| 5,565,105 A | * | 10/1996 | Thakor ....................... 210/695 |
| 5,858,199 A | | 1/1999 | Hanak |
| 6,019,455 A | | 2/2000 | Taylor et al. |
| 6,277,258 B1 | * | 8/2001 | Ivory et al. .................. 204/450 |
| 2003/0094369 A1 | * | 5/2003 | Tolley et al. ............... 204/450 |

FOREIGN PATENT DOCUMENTS

| | | |
|---|---|---|
| DE | 198 60 118 C1 | 9/2000 |
| WO | WO 00/00292 A1 | 1/2000 |
| WO | WO 01/06228 A3 | 1/2001 |
| WO | WO 01/06228 A2 | 1/2001 |

* cited by examiner

Primary Examiner—Jeffrey R. Snay
(74) Attorney, Agent, or Firm—Wallenstein Wagner & Rockey, Ltd.

(57) ABSTRACT

A centrifugal spectrometer has a solid rotor (10) formed within which there are cavities or blades (12). In use, each blade is filled with a buffer solution, and a sample to be separated is placed in a sample well (32) at the end of a separation channel (24). The rotor is spun at a controlled velocity and, at the same time, a controlled potential difference is applied along the length of the blade. The blade shape causes the resultant electric field to vary as a function of radial distance. The sample separates out into bands, which move along the channel (24) under the combined influence of the centrifugal force and the varying electric field. The bands focus at differing equilibrium points according to their charge/mass ratios. The band positions are determined by a readout head (36). The dynamic range of the device may be controlled by altering the rotational velocity and the voltages that are applied.

50 Claims, 6 Drawing Sheets

US 6,893,878 B2

CENTRIFUGAL SPECTROMETER

TECHNICAL FIELD

The present invention relates to a centrifugal spectrometer, and in particular although not exclusively to a spectrometer for separating biological cells, macromolecules or other objects. The invention further relates to the general fields of the sequencing and sorting of biomolecules, and the sorting of cells.

BACKGROUND OF THE INVENTION

Conventionally, the sequencing and sorting of biomolecules, and the sorting of cells, is carried out using electrophoresis. A variety of different approaches are possible, but most take a considerable amount of time to run to completion. Furthermore, a balance has to be struck between reading out the results relatively quickly (when the bands will be narrow but very close together) and delaying the readout (in which case the bands, although further apart, will have become broader and more diffuse).

SUMMARY OF THE INVENTION

It is an object of the present invention at least to alleviate these difficulties of the prior art.

It is a further object of the invention to provide a spectrometer, and a method of separating objects, which is simple, convenient and quick to use.

According to a first aspect of the present invention there is provided a method of separating objects comprising (a) placing the objects in a separation channel;
(b) rotating the channel to produce a centrifugal force on the objects;
(c) creating an electric field which varies along the channel; and
(d) allowing the objects to migrate and separate along the channel under the combined influences of the centrifugal force and the electric field.

According to a further aspect of the invention, there is provided a spectrometer rotor, comprising:

(a) a radially-extending blade;
(b) field shaping means for shaping an electric field which, in use, varies along the blade;

whereby when the rotor is rotated about an axis, objects within the blade migrate and separate under the combined influence of the centrifugal force and the electric field.

The invention further extends to a spectrometer including a spectrometer rotor as previously defined. The spectrometer may include a controller for simultaneously controlling one or both of the rotor angular velocity and the electric field. Preferably, the controls may be linked in order to allow the user to vary the dynamic range of the spectrometer.

The invention provides superiority over conventional methods of electrophoresis, due to the fact that it focuses the separated bands (within potential wells) so that they do not broaden with time. This gives the advantage of extra resolution. The method and apparatus of the present invention also provides greater throughput and dynamic range, in addition to having the capability, in some embodiments, of variable dynamic range.

Where more than one blade is provided on the rotor, native and SDS-page treated protein samples may be separated out, in parallel, thereby providing an alternative to a conventional 2-D protein map. There is a substantial advantage in speed.

The invention may be used to carry out DNA sequencing and analysis of single nucleotide polymorphisms, using some relatively simple sample preparations. The method and apparatus of the present invention may be able to resolve longer DNA chains than can conventional sequencers.

The present invention is also expected to be extremely effective in cell sorting, since it operates very rapidly compared with conventional cell sorters.

The invention, in some embodiments, also allows for the possibility of extracting interesting identified bands (of cells, proteins, DNA or other objects being separated) for further analysis.

In most embodiments, the objects to be separated migrate through a liquid buffer (for example saline solution) under the combined influence of the centrifugal force and the electric field. Other embodiments are however envisaged in which molecules or other objects to be separated migrate through a gaseous buffer, or move within a vacuum cavity.

In addition to being used for the selection, sorting and where appropriate sequencing of biomolecules such as DNA, RNA, proteins and so on, the invention may also be applied to the separation of biological cells, gas or vapor molecules, along with a variety of other small objects such as particulates. It could be used to sort any objects with well-defined q/m values.

BRIEF DESCRIPTION OF THE DRAWINGS

The invention may be carried into practice in a number of ways, and a variety of specific embodiments will now be described, by way of example, with reference to the accompanying drawings, in which.

DETAILED DESCRIPTION OF THE PREFERRED EMBODIMENT

Figure 1:
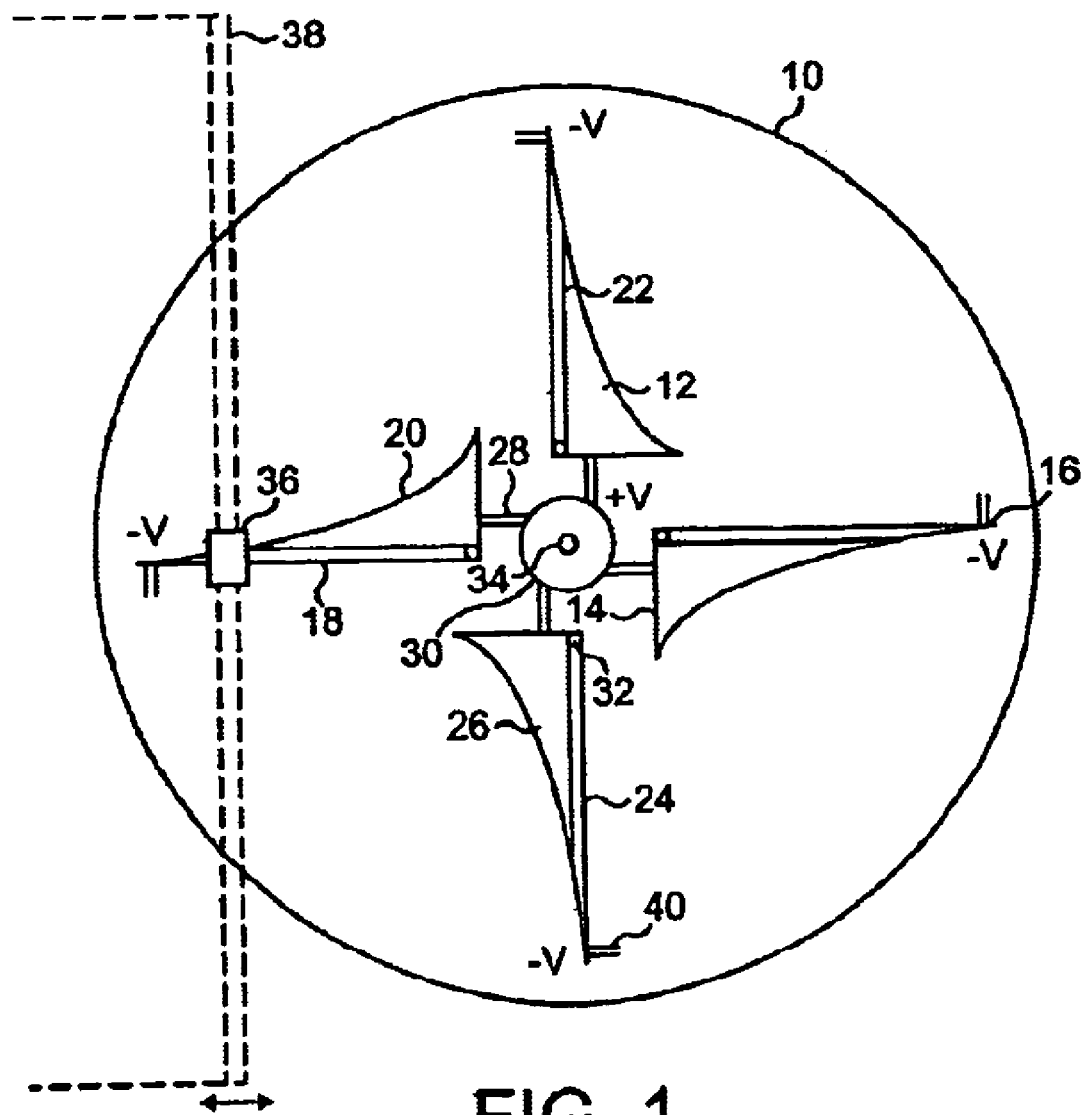
FIG. 1 shows the rotor of a spectrometer according to a first embodiment of the invention.

FIG. 1 illustrates, schematically, the rotor of a spectrometer according to a first embodiment of the invention. The rotor consists of a flat, round, disk or platform of a rigid material (such as steel), within which is cut a number of circumferential-vertical-sided cavities or blades 12. In FIG. 1, four blades are shown, but there may be more or fewer than that number.

Each blade extends radially from a flat inner edge 14 to a blade end 16 near the outer periphery of the disk 10. One side of the blade is defined by a straight edge 18, while the other is defined by a shaped edge 20. Within the cavity 12 there is a vertical wall, parallel with the straight edge 18, which separates the cavity into two portions, namely a narrow separation channel 24 and a buffer (e.g. saline solution) region 26. A small aperture or gap (not shown) is provided somewhere along the length of the wall, allowing communication between the separation channel 24 and the buffer region 26, so that in use the former also contains buffer. Feed channels 28 connect each of the buffer regions 26 with a central well 30. UV-transparent covers (not shown) are bonded to the upper and lower surfaces of the disk 10, thereby enclosing the cavities. The covers may be entirely transparent or, alternatively, may be transparent only above and below the separation channels 24, thereby defining four narrow radially-extending readout strips. Where appropriate, to maintain electrical isolation, the walls of the cavities may be coated with a non-conductive material.

To prepare the rotor for use, a conductive buffer (e.g. a saline solution) is introduced into the central well 30 through a central hole (not shown) in the upper cover, and is allowed to pass down the feed channels 28 into the buffer regions 26. From there, the solution passes through the gap in the wall to fill the separation channels 24. Samples containing biomolecules, cells or other objects for separation are placed in wells 32 at the inner end of each of the separation channels 24. Small holes (not shown) in the upper cover provide access to these wells.

In order to start the separation process, the disk 10 is rapidly spun, at a controlled angular velocity, around a central spindle 34. Simultaneously, a radial potential difference is applied to the buffer solution within each blade, preferably by applying a positive voltage at the inner edge 14 and a negative voltage at the blade end 16. To achieve that, an electrode (not shown) is provided at the blade end, and another electrode (not shown) coats the surface of the inner edge 14.

The objects to be separated move from the well 32 along the separation channel 24 under the influence of two separate forces, namely a centrifugal force $F=mr\omega^2$ and an electric force. The centrifugal force varies with r along the length of the channel, provided that the rotational velocity is not changed, but the electric force does not. Because of the shape of the edge 20, the electric field within the cavity varies non-linearly with radial distance. Since the wall 22 has little or no effect on the electric field within the cavity, the field within the separation channel 24 is substantially the same as that within the buffer region 26 (i.e. the isopotential lines extend across the wall 22). Thus, the objects being separated experience an electric force which varies non-linearly according to the distance the object has travelled down the channel, with the relationship between the distance and the force being defined by the precise configuration of the shaped edge 20. It will be understood that the purpose of the wall is merely to prevent the sample from diffusing across into the buffer region 26, and to keep it closely constrained within a linear channel from which readouts can easily be taken.

Depending upon the voltages applied, the speed of rotation, and the configuration of the shaped edge 20, the molecules or other objects being separated move along the channels until they reach the bottom of a potential well in which the outward centrifugal force exactly balances the inward force due to the electric field. As will be shown in more detail below, the equilibrium point for a particular object depends upon its effective charge/mass ratio q/m within the buffer environment. Hence, the sample automatically separates out into a number of different bands, each representing a particular q/m value. Because the positions of the bands are defined by the lowest points of potential wells, the band widths remain constant once equilibrium has been achieved, and do not substantially diffuse with time.

In order to read out the band positions, a read head 36 is employed, the head 10 being mounted for radial movement across the disk on a movable head positioner 38. Alternatively, the head may be elongated, and fixed. The head reads the position of the bands by any convenient mechanism, such as by detecting band fluorescence, which may be intrinsic to the molecule or induced by a laser or other light source. It is preferred, however, that the head consists of a UV detector arranged to detect the intrinsic UV absorption of the bands. That may be achieved by allowing a UV light (not shown) to shine through the UV-transparent lower cover, through the sample, and through the UV-transparent upper cover prior to detection by the head 36. By determining the amount of light received by the head, the amount of UV that has been absorbed by the sample can be determined.

The illumination could be uniform across the disk, or it could be selective (e.g. applied to one band or to a group of bands only) and under computer control.

Figure 11:
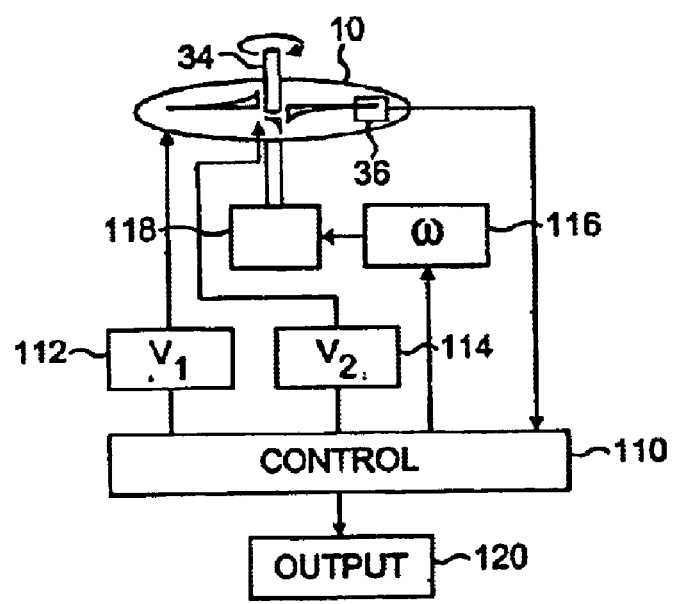
FIG. 11 shows, schematically, an exemplary spectrometer control system.

Turning now to FIG. 11, there is shown an exemplary spectrometer control system for use with a rotor such as that shown in FIG. 1. A spectrometer control 110, for example a micro-computer, controls first and second voltage regulators 112,114, which respectively supply the voltages to the outer and inner ends of the blades. The control 110 also controls a rotational controller 116 which itself regulates the rotational speed of a variable-speed motor 118 which spins the disk 10. The readout from the head 36 is supplied to the controller 110 allowing, if desired, the rotational velocity and the voltages to be adjusted either automatically or by a user in dependence upon the measured band positions. The spectrometer supplies information on the measured band positions to an output 120, for example to a computer screen or to a data capture system.

By manually or automatically varying the voltages and, at the same time, the rotational speed of the disk, the spectrometer may be tuned to resolve bands over different q/m ranges. As will be shown in more detail below appropriate voltage and/or rotational speed changes allow the user to adjust not only the precision of the device (the width of the q/m range that can be measured), but also the starting point of that range. To put it another way, both the size and the position of the q/m "window" that the spectrometer is sensitive to can be varied.

Once a particular band of interest has been detected by the system, the voltages and/or the rotational speed may be varied as required to move that band, under automatic or user control, to a collection point or channel 40 (FIG. 1) near the blade end 16. The selected sample band may then be manually or automatically collected from that point, for further investigation.

As mentioned above, the shape of the field within each blade, and hence the variation in field strength with distance along the separation channel, is determined by the blade shape. This need not be the same as that shown in FIG. 1, but may be chosen according to the application in hand and, in particular, on the characteristics of the molecules, cells or other objects that are to be separated. Preferably, though, the field shaping is such that the electric force varies with a power of r which is greater than 1.

We now turn to a brief review of some of the considerations which will determine the shape. First, we recall that at the equilibrium point there must be equality between the centrifugal and the electric force. The centrifugal force on a molecule of mass m at radial distance r from the rotation axis is:

$$F_c = -m\omega^2 r \quad (1)$$

The Electric field applied to the ends of the rotor blade is defined as:

$$F_e = +q(kr^2 + C) \quad (2)$$

where q is the apparent charge of the molecule, k a positive factor that defines the size of the electric field and C is the dilution factor of the field, that is how big the linear deviation is from the square dependence on the radius. This constant is useful in order to have freedom to create a rotor blade of a reasonable shape. It should be noted that the square term is nominal and that similar considerations apply with any power ($\geq 1$) in the r term.

The total force on a molecule from (1) and (2) is:

$$F = F_c + F_e = q(kr^2 + C) - m\omega^2 r \quad (3)$$

Here we ignore the buoyance effect of the buffer. This factor is a force opposing the centrifugal force. The total force is equal to the centrifugal force on a molecule with mass $rn - rn_0$ where rn is the mass of the molecule and $rn_0$ is the mass of the buffer displaced by one separating molecule. This assumes a buffer of constant density (not a problem, in practice).

At equilibrium, from (3):

$$q(kr^2 + C) - rn\omega^2 r = 0 \quad (4)$$

which gives:

$$r_{eq} = \frac{m\omega^2 \pm \sqrt{m^2\omega^4 - 4q^2 Ck}}{2qk} \quad (5)$$

The negative solution corresponds to an unstable equilibrium and can be ignored. Eq. (5) can also be rewritten as:

$$r_{eq} = \left[\frac{m}{q}\right]\frac{\omega^2}{2k} \pm \sqrt{\left[\frac{m}{q}\right]^2 \frac{\omega^4}{4k^2} - \frac{C}{k}} \quad (6)$$

which reveals the charge to mass dependence of the equilibrium.

According to eq (2) we want to achieve the electric field:

$$E(r) = kr^2 + C \quad (7)$$

The electric field can be written as a function of the electric potential at r, V(r) using r=0 as a reference point:

$$E(r) = \frac{dV(r)}{dr} = i\frac{dR(r)}{dr} \quad (8)$$

where i is the electric current in the blade and R the electric resistance. We define as p the buffer resistivity (e.g. measured $-82 \, \Omega rn$ for 1×TBE buffer).

In the following analysis, we achieve our desired field shape by suitable selection of the shape of the wall 20 (FIG. 1). The necessary fields could also be generated by shaping electrodes suitably positioned along the length of the rotor blades.

We can write:

$$\frac{dR(r)}{dr} = \frac{\rho}{Dw(r)} \quad (9)$$

where w(r) is the width of the blade at r and D the depth of the blade. From Eqs 7,8,9 we derive w(r):

$$w(r) = \frac{i\rho}{D(kr^2 + C)} \quad (10)$$

At the maximum separation distance $r_2$ we have $w(r_2) = w_2$ and at the minimum radius $r_1$ we have $w(r_1) = w_1$. From eq. (10) we have:

$$k = i\frac{\rho}{D}\frac{w_2^{-1} - w_1^{-1}}{r_2^2 - r_1^2} \quad (11)$$

$$C = i\frac{\rho}{D}w_2^{-1} - kr_2^2$$

The total resistance of the blade is:

$$R(r_2) = \int_{r_1}^{r_2} \frac{dR(r)}{dr} dr = \frac{1}{i}\int_{r_1}^{r_2}(kr^2 + C)dr \quad (12)$$

The voltage at the two ends of the blade is V=i R and from (12) we get:

$$V = \frac{1}{3}k(r_2^3 - r_1^3) + C(r_2 - r_1) \quad (13)$$

Finally we can calculate the potential well which will be created for the above values:

$$W(r) = \int_{r_1}^{r} F(r) dr = \int_{r_1}^{r}(qkr^2 + qC - m\omega^2 r^2)dr \Rightarrow \quad (14)$$

$$W(r) = \frac{1}{3}qk(r^3 - r_1^3) + qC(r - r_1) - \frac{1}{2}m\omega^2(r^2 - r_1^2)$$

One possible configuration is as follows:

| Outer Width $w_2$ (mm) | Inner Width $w_1$ (mm) | Outer Radius $r_2$ (mm) | Inner Radius $r_1$ (mm) |
|---|---|---|---|
| 1 | 20 | 150 | 10 |

| Angular Velocity $\omega$ (rpm) | Buffer Resistivity $\rho$ ($\Omega$ m) | Voltage V (V) | Current i ($\mu$A) |
|---|---|---|---|
| 3000 | 82 | 3000 | 1102 |

All of the numbers in the above table, apart from the current, are user-selected. The current is calculated from equation (13) and Ohm's law.

Figure 4:
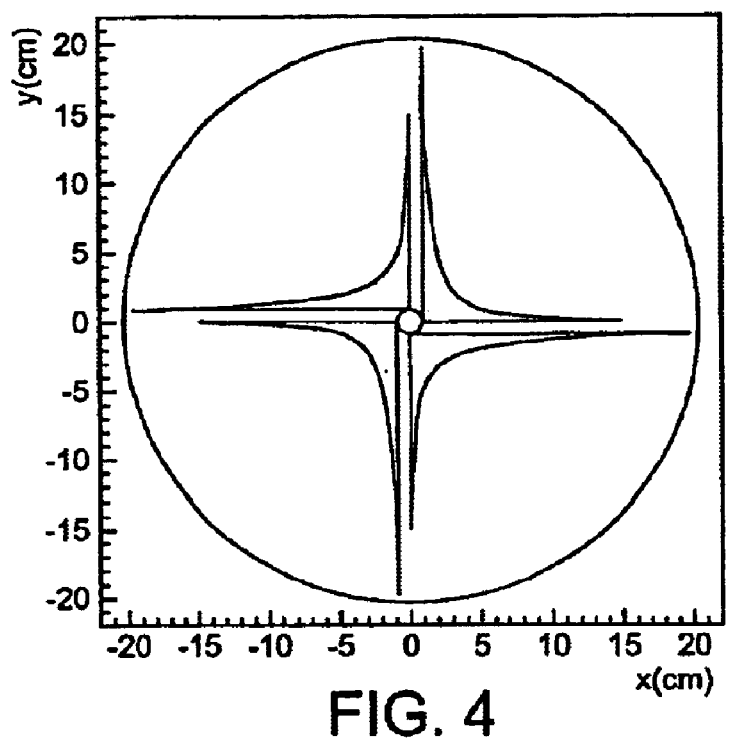
FIG. 4 shows an alternative rotor configuration, similar to that of FIG. 1.

FIG. 4 shows the rotor shapes for the configuration parameters set out above. In this example, there are four blades, each having a separation channel 1 mm wide and 15 mm long.

Figure 5:
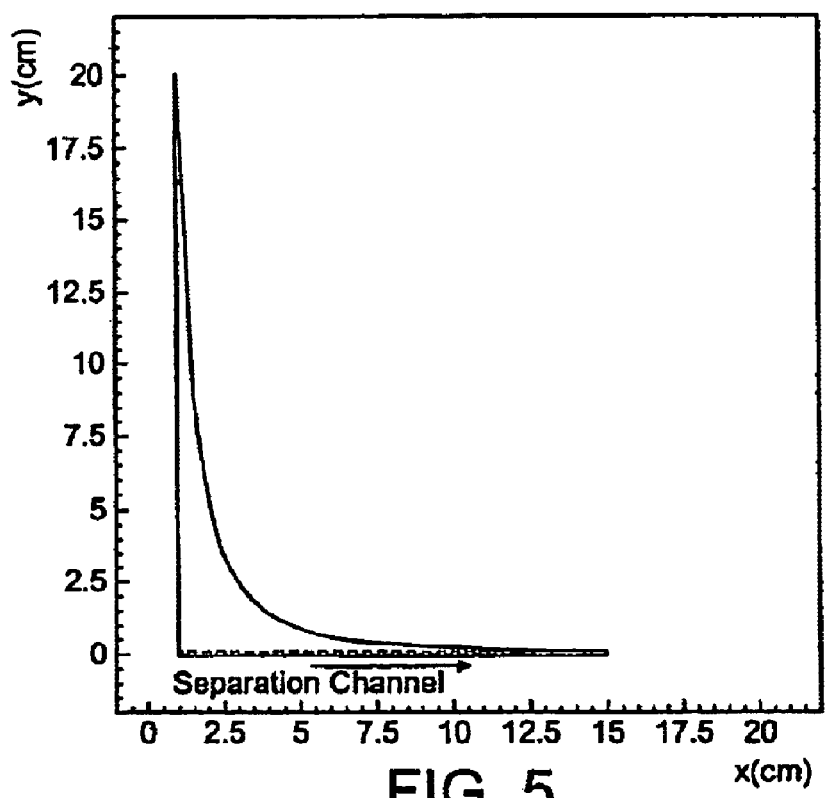
FIG. 5 shows in more detail the shape of one of the rotor blades of FIG. 4.

FIG. 5 shows in more detail the exact shape of one of the blades, in this configuration.

Figure 6:
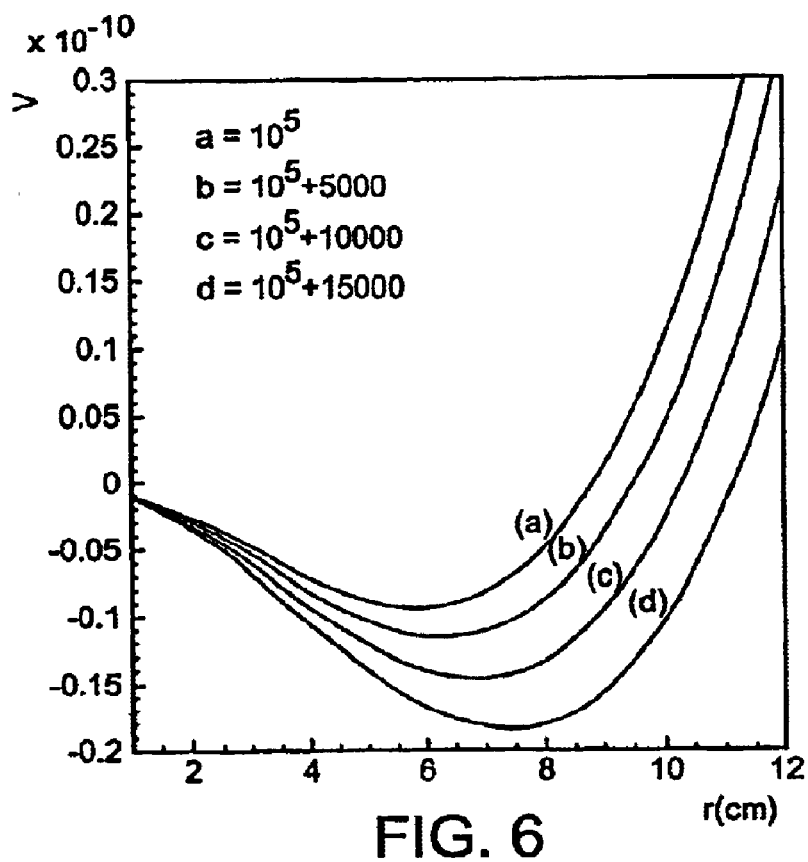
FIG. 6 shows the potential wells as a function of radius, for the 10 configuration of FIG. 4.

FIG. 6 shows the potential wells for this configuration, in Joules, as a function of radius. The shallowest curve corresponds to a q/m value of $10^5$ (in SI units), with the deepest corresponding to $10^5+15{,}000$.

Figure 7:
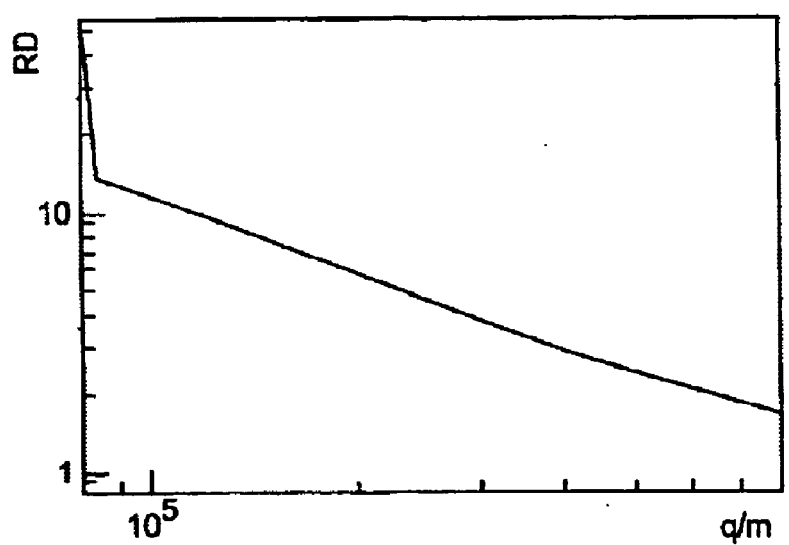
FIG. 7 shows the distribution of the equilibrium points for a given q/m range, for the configuration of FIG. 4.

FIG. 7 shows the distribution of the equilibrium points for the given q/m range.

We now turn to a consideration of the expected resolution of the bands. This of course will depend upon temperature. Let us assume, for the sake of simplicity, that the sample acts like a gas, and that the thermal energy can be described by:

$$E = \frac{3}{2}kT \quad (15)$$

where T is the temperature and k the Boltzman constant. One way to get an idea of the band broadening, induced by the thermal movement, is to see how far from the equilibrium point a molecule can move for a given thermal energy E.

Figure 8:
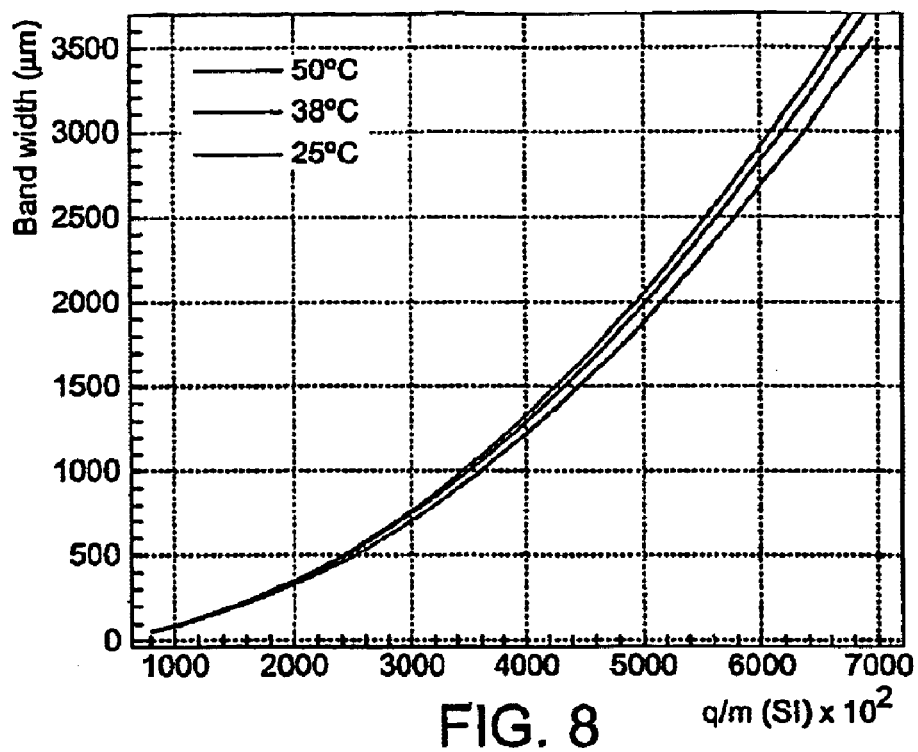
FIG. 8 shows the q/m dependence of bandwidth for a variety of different temperatures.

To calculate this we could solve eq (14) for r, where $r_1$ would correspond to the equilibrium point and W to the thermal energy, thus W=E. FIG. 8 shows estimates of the bandwidth, for different values of q/m, at the sample temperatures 25° C., 38° C. and 50° C. It will be seen that there is little change between 25° C. and 50° C.

Figure 9:
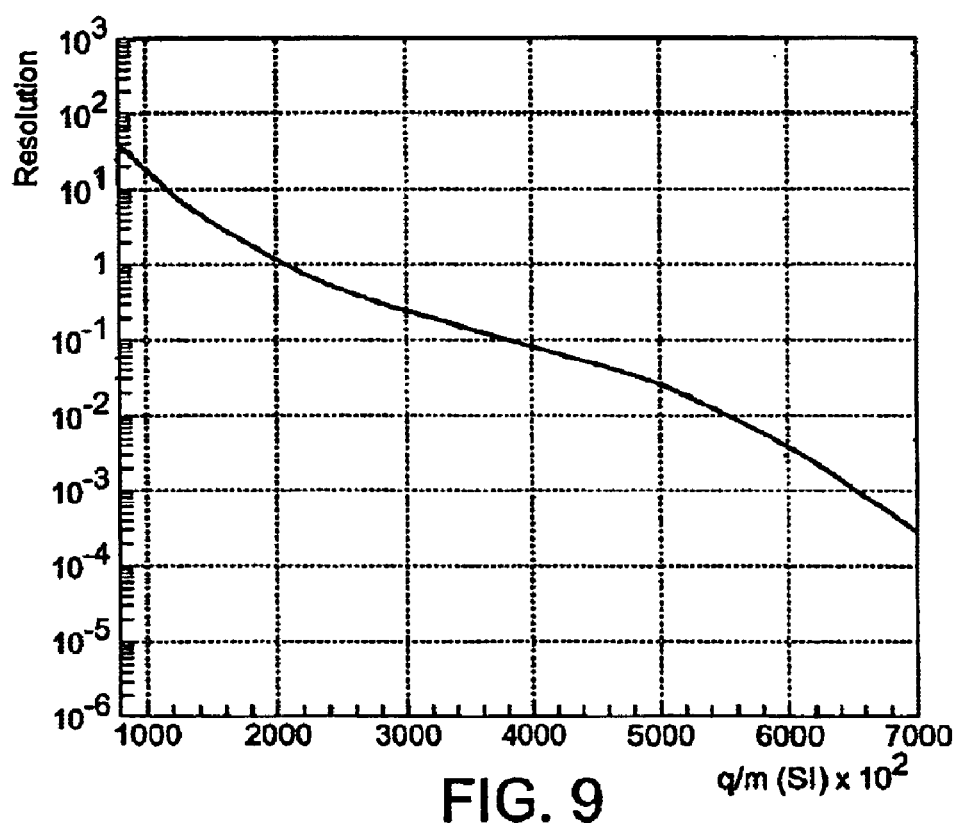
FIG. 9 illustrates how well neighboring q/m values can be resolved, as a function of q/m.

To estimate how well we can resolve neighboring q/m values, we can study how far apart q/m and q/m+1400 are for various q/m. This is shown in FIG. 9.

Figure 10:
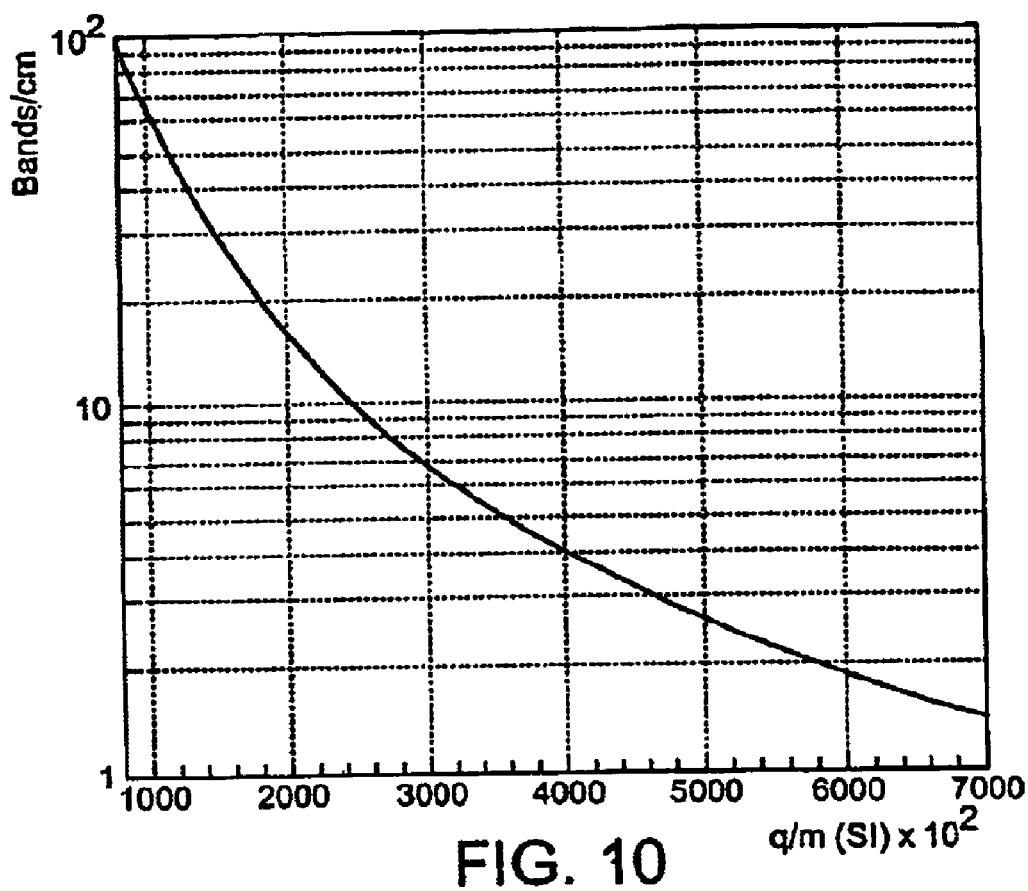
FIG. 10 shows how many bands per centimetre can be resolved as a function of q/m at 25° C.

Finally FIG. 10 shows us how many bands per cm we could resolve assuming they have to be apart by one band width to be resolved.

We can conclude from the above that using a blade configuration as shown in FIG. 4, along with the parameters mentioned, we can produce the necessary electric fields to separate out protein molecules in a ph environment ranging from 5–10. The potential wells are deep enough to achieve very good band resolution over a large fraction of the length of the blade.

Shaping of the blade edges is not the only way to create an electric field which varies along the length of the separation channel. An alternative approach is shown in the embodiment of FIG. 2, in which similar parts are labeled with the same reference numerals as those previously used for FIG. 1.

Figure 2:
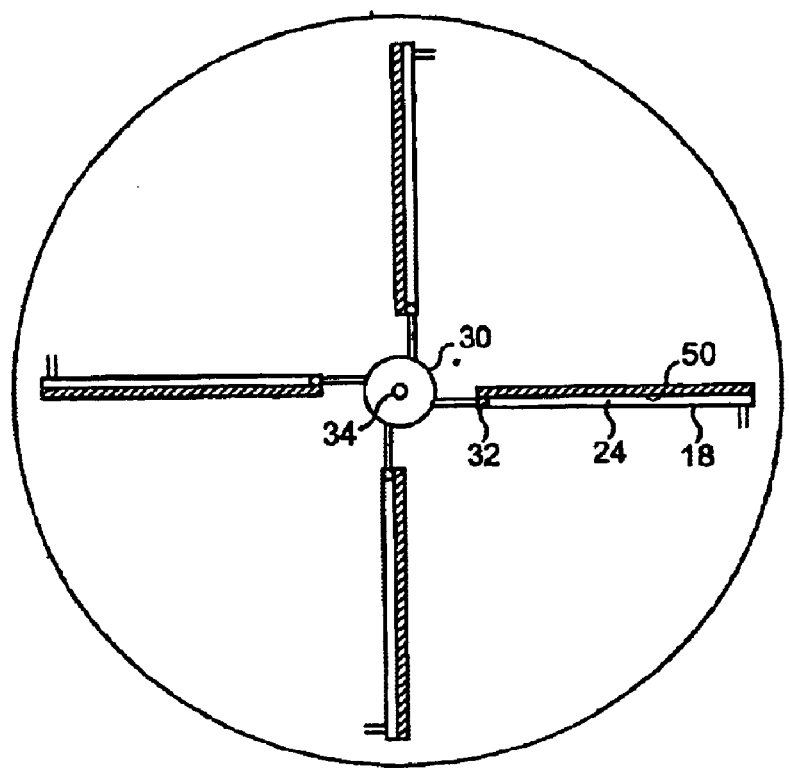
FIG. 2 shows an alternative rotor of a second embodiment.

In the FIG. 2 embodiment, the buffer regions of the blades, and the shaped edge 20, are replaced with a variable-resistance wall 50 which defines one side of the separation channels 24. By varying the way in which the resistance of the wall varies with radial distance, the manner in which the electric field varies with distance can also be altered.

Figure 3:
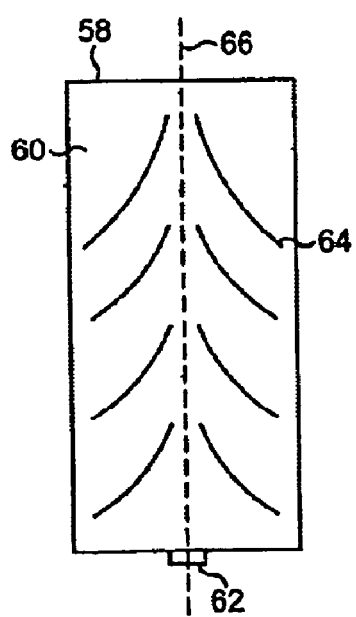
FIG. 3 shows the cavity for a rotor according to a third embodiment.

Another embodiment is shown schematically in FIG. 3. In this embodiment, a vapor or gas is to be separated, rather than a liquid, and the separation channel is replaced by a sealed vacuum chamber 58. A gas sample for study is introduced into the volume 60 of the chamber by a sample introducing means 62 at an end of the chamber adjacent to the rotation axis. The gas sample migrates in the vacuum along a radial axis 66 under influence of both the centrifugal force and an electric field generated by field-shaping wires 64. The shape and configuration of the wires 64 are chosen so that the field varies with radial position in the required way. As with the liquid case, any convenient mechanism may be used for readout, including the intrinsic UV absorption of the gas or vapour sample itself.

Field-shaping wires could, similarly, be used to provide a graduated field in the FIG. 2 embodiment (instead of the variable-resistance wall 50). A graduated field could be produced by unevenly-spaced wires or electrodes with equal potential differences between adjacent electrodes, or by evenly-spaced wires or electrodes with unequal potential differences.

Although it may be convenient for the blades and the separation channels to be cut or otherwise formed within the body of a disk 10, it will of course be understood that there are numerous other manufacturing possibilities. Each blade may for example be manufactured separately, with the blades then being mounted to a common support to provide rigidity during rotation. There could be more or fewer blades than shown in the drawings; the system is constrained only by the mechanical robustness of the centrifuge.

The rotor may be of a suitable size and shape to be received within a standard (speed-controllable) centrifuge. The mechanism for positioning the readout head could be similar or identical to that used in conventional CD players.

In addition to varying the field strengths with radial position, the effective centrifugal force along the length of the separation channel 24 could also be varied with radial position (to a power other than 1) by making the channel curved. In a curved channel, the resolved centrifugal force tending to move the sample along the channel will depend upon the angle the channel makes with the radial direction. By varying that angle with radial distance, the resolved force will also vary with radial distance (or, equivalently, distance along the channel).

Depending upon the sample to be investigated, some pre-treatment may be desirable. For example, to separate DNA fragments, it may be desirable to add a fixed large mass to each fragment, to ensure that the q/m values differ. A constant charge (e.g. +1) could also be applied to each object in the sample, for example to each protein. If the charge on each object is always the same, the spectrometer will give a direct readout of mass.

The invention claimed is:

1. A method of separating objects comprising:
    (a) placing the objects in a separation channel;
    (b) rotating the channel to produce a centrifugal force on the objects;
    (c) applying, by means of field-shaping electrodes disposed along the channel, an electric field which varies with a power of r which is greater than or equal to 1, wherein r is a distance along the channel; and
    (d) allowing the objects to migrate and separate along the channel under the combined influences of the centrifugal force and the electric field.

2. The method as claimed in claim 1 further comprising, during step (d):
    (e) dynamically varying the applied electric field so as to control the migration of the objects during separation.

3. The method as claimed in claim 1 or claim 2 in which the objects are biomolecules.

4. The method as claimed in claim 3 in which the objects are proteins.

5. The method as claimed in claim 3 in which the objects are either DNA or RNA fragments.

6. The method as claimed in claim 1 or claim 2 in which the objects are biological cells.

7. The method as claimed in claim 1 or claim 2 in which the objects are either gas or vapor molecules.

8. The method as claimed in claim 1 or claim 2 in which the objects migrate to respective equilibrium points at which the centrifugal force is equal to an opposing force due to the electric field.

9. The method as claimed in claim 1 or claim 2 further including controlling the migration of the objects by varying an angular velocity at which the channel is rotated.

10. The method as claimed in claim 1 or claim 2 further including controlling the migration of the objects by controlling first and second voltages applied respectively at a first end of the channel and at a second end.

11. The method as claimed in claim 9 in which the migration of the objects is controlled in order to move an object of interest to a collection point from which it may be collected for further study.

12. The method as claimed in claim 10 in which the migration of the objects is controlled in order to move an object of interest to a collection point from which it may be collected for further study.

13. A method of separating objects comprising:
(a) placing the object in a separation channel;
(b) rotating the channel to produce a centrifugal force on the objects;
(c) applying, by means of the cavity having a width which varies along its length, an electric field which varies with a power of r which is greater than or equal to 1, wherein r is a distance along the channel; and
(d) allowing the objects to migrate and separate along the channel under the combined influences of the centrifugal force and the electric field.

14. The method as claimed in claim 13 in which the objects are biomolecules.

15. The method as claimed in claim 14 in which the objects are proteins.

16. The method as claimed in claim 14 in which the objects are either DNA or RNA fragments.

17. The method as claimed in claim 13 in which the objects are biological cells.

18. The method as claimed in claim 13 in which the objects are either gas or vapor molecules.

19. The method as claimed in claim 13 in which the objects migrate to respective equilibrium points at which the centrifugal force is equal to an opposing force due to the electric field.

20. The method as claimed in claim 13 further including controlling the migration of the objects by varying an angular velocity at which the channel is rotated.

21. The method as claimed in claim 13 further including controlling the migration of the objects by controlling first and second voltages applied respectively at a first end of the channel and at a second end.

22. The method as claimed in claim 20 in which the migration of the objects is controlled in order to move an object of interest to a collection point from which it may be collected for further study.

23. The method as claimed in claim 21 in which the migration of the objects is controlled in order to move an object of interest to a collection point from which it may be collected for further study.

24. A method of separating gas or vapor molecules comprising:
(a) placing the molecules in a vacuum chamber;
(b) rotating the vacuum chamber to produce a centrifugal force on the molecules;
(c) applying an electric field which varies with a power of r which is greater than or equal to 1, wherein r is a distance along the vacuum chamber; and
(d) allowing the molecules to migrate and separate along the vacuum chamber under the combined influences of the centrifugal force and the electric field.

25. The method as claimed in claim 24 in which the molecules migrate to respective equilibrium points at which the centrifugal force is equal to an opposing force due to the electric field.

26. The method as claimed in claim 24 further including controlling the migration of the molecules by varying an angular velocity at which the vacuum chamber is rotated.

27. The method as claimed in claim 24 further including controlling the migration of the molecules by controlling first and second voltages applied respectively at a first end of the vacuum chamber and at a second end.

28. The method as claimed in claim 26 in which the migration of the molecules is controlled in order to move an object of interest to a collection point from which it may be collected for further study.

29. The method as claimed in claim 27 in which the migration of the molecules is controlled in order to move an object of interest to a collection point from which it may be collected for further study.

30. A rotor for a separating device comprising:
(a) a radially extending cavity, and
(b) field shaping electrodes disposed along the cavity for shaping an electric field which, in use, varies with a power of r which is greater than or equal to 1, wherein r is a distance along the cavity,
whereby when the rotor is rotated about an axis, objects within the cavity migrate and separate under the combined influence of the centrifugal force and the electric field.

31. A The rotor for a separating device as claimed in claim 30 further comprising a controller for controlling the field shaping electrode so as to dynamically vary the applied electric field during separation of the objects.

32. The rotor for a separating device as claimed in claim 30 in which the cavity is defined within a disk-like rotor body.

33. The rotor for a separating device as claimed in claim 30 including a collection point on the cavity from which selected separated objects may be collected.

34. The rotor for a separating device as claimed in claim 30 in which the cavity is arranged for receipt of objects for separation within a liquid or gaseous buffer.

35. A rotor for a separating device comprising:
(a) a radially extending cavity which has a width which varies along its length, and
(b) field shaping means which include a first electrode for applying a first voltage at a first end of the cavity and a second electrode for applying a second voltage at a second radially spaced end of the cavity,
whereby when the rotor is rotated about an axis, objects within the cavity migrate and separate under the combined influence of the centrifugal force and the electric field.

36. The rotor for a separating device as claimed in claim 35 in which the cavity comprises a parallel-sided separation channel and a variable-width buffer region, the separation channel being arranged, in use, to receive the objects to be separated.

37. The rotor for a separating device as claimed in claim 35 in which the cavity is defined within a disk-like rotor body.

38. The rotor for a separating device as claimed in claim 35 including a collection point on the cavity from which selected separated objects may be collected.

39. The rotor for a separating device as claimed in claim 35 in which the cavity is arranged for receipt of objects for separation within a liquid or gaseous buffer.

40. A rotor for a separating device comprising:
(a) a radially extending vacuum chamber, and
(b) field shaping means for shaping an electric field which, in use, varies with a power of r which is greater than or equal to 1, wherein r is a distance along the vacuum chamber, whereby when the rotor is rotated about an axis, gas or vapor molecules within the chamber migrate and separate under the combined influence of the centrifugal force and the electric field.

41. The rotor for a separating device as claimed in claim 40 in which the field shaping means include a first electrode for applying a first voltage at a first end of the vacuum chamber and a second electrode for applying a second voltage at a second radially spaced end of the vacuum chamber.

42. The rotor for a separating device as claimed in claim 40 in which the vacuum chamber is defined within a disk-like rotor body.

43. The rotor for a separating device as claimed in claim 40 including a collection point on the vacuum chamber from which the selected separated molecules may be collected.

44. The rotor for a separating device as claimed in claim 40 in which the field shaping means includes shaping electrodes within the vacuum chamber.

45. The rotor for a separating device as claimed in claim 40 in which the cavity is arranged for receipt of molecules for separation within a gaseous buffer.

46. A separating device comprising a rotor as claimed in claim 30, claim 35, or claim 40 in combination with a motor and motor control for controlling rotor angular velocity.

47. The separating device as claimed in claim 46 further including means for generating and controlling the electric field.

48. The separating device as claimed in claim 46 further including a controller for simultaneous controlling both the rotor angular velocity and the electric field.

49. The separating device as claimed in claim 47 further including means for applying user-defined voltages to both the first and second electrodes.

50. The separating device as claimed in claim 49 further including a controller for simultaneously controlling the first and second voltages and the rotor angular velocity.

* * * * *